US012564439B2

(12) United States Patent
Avalos

(10) Patent No.: US 12,564,439 B2
(45) Date of Patent: Mar. 3, 2026

(54) ENDOSCOPE LASER-TRIGGERED SUCTION AUTOMATIC ON/OFF

(71) Applicant: GYRUS ACMI, INC., Westborough, MA (US)

(72) Inventor: Jordan C. Avalos, Littleton, MA (US)

(73) Assignee: Gyrus ACMI, Inc., Westborough, MA (US)

( * ) Notice: Subject to any disclaimer, the term of this patent is extended or adjusted under 35 U.S.C. 154(b) by 567 days.

(21) Appl. No.: 18/047,606

(22) Filed: Oct. 18, 2022

(65) Prior Publication Data

US 2023/0130679 A1      Apr. 27, 2023

Related U.S. Application Data

(60) Provisional application No. 63/262,924, filed on Oct. 22, 2021.

(51) Int. Cl.
| | |
|---|---|
| *A61B 18/14* | (2006.01) |
| *A61B 1/00* | (2006.01) |
| *A61B 1/015* | (2006.01) |
| *A61B 18/26* | (2006.01) |
| *A61B 18/00* | (2006.01) |

(52) U.S. Cl.
CPC .... *A61B 18/1492* (2013.01); *A61B 1/000096* (2022.02); *A61B 1/015* (2013.01); *A61B 18/26* (2013.01); *A61B 2018/00577* (2013.01); *A61B 2018/00744* (2013.01); *A61B 2018/00791* (2013.01); *A61B 2018/00982* (2013.01); *A61B 2218/002* (2013.01); *A61B 2218/007* (2013.01)

(58) Field of Classification Search
None
See application file for complete search history.

(56) References Cited

U.S. PATENT DOCUMENTS

| | | | |
|---|---|---|---|
| 9,066,658 B2 * | 6/2015 | Hamel | A61B 1/045 |
| 9,500,473 B2 | 11/2016 | Ramamurthy et al. | |
| 10,499,936 B2 | 12/2019 | Harrah et al. | |
| 11,246,643 B2 * | 2/2022 | Cheng | A61B 18/1206 |

(Continued)

FOREIGN PATENT DOCUMENTS

| | | |
|---|---|---|
| CN | 108601622 A | 9/2018 |
| CN | 110811826 A | 2/2020 |

(Continued)

OTHER PUBLICATIONS

"Indian Application Serial No. 202244060600, First Examination Report mailed Jan. 10, 2024", 6 pgs.

(Continued)

*Primary Examiner* — John P Leubecker

(74) *Attorney, Agent, or Firm* — Schwegman Lundberg & Woessner, P.A.

(57) ABSTRACT

A suction or other component of an endoscope system may be cycled on and off or otherwise controlled without requiring direct user input, such as automatically or semi-automatically using a current or historical state of a laser generator, a blurriness or other information from an image of the working area, a count of fragments of a calculi stone, an intraoperative pressure, an intraoperative temperature, or one or more other characteristics of the laser generator or the targeted calculi stone.

30 Claims, 5 Drawing Sheets

(56) References Cited

U.S. PATENT DOCUMENTS

| | | | | |
|---|---|---|---|---|
| 2003/0009085 A1 | | 1/2003 | Arai et al. | |
| 2016/0166320 A1* | | 6/2016 | Ciulla | A61B 18/26 |
| | | | | 606/14 |
| 2017/0007310 A1* | | 1/2017 | Rajagopalan | A61B 5/0084 |
| 2017/0181794 A1* | | 6/2017 | Govari | A61B 18/1492 |
| 2017/0215965 A1 | | 8/2017 | Harrah et al. | |
| 2017/0333614 A1* | | 11/2017 | Gao | A61B 18/26 |
| 2018/0055568 A1* | | 3/2018 | Shelton | A61B 1/00009 |
| 2020/0187768 A1 | | 6/2020 | Shelton et al. | |
| 2020/0405378 A1* | | 12/2020 | Bagrosky | A61B 34/37 |
| 2021/0085165 A1* | | 3/2021 | Rauniyar | A61M 3/0204 |
| 2021/0236728 A1 | | 8/2021 | Fanning et al. | |
| 2022/0202285 A1 | | 6/2022 | Bukesov et al. | |
| 2022/0265121 A1* | | 8/2022 | Fouts | A61B 1/317 |
| 2022/0354352 A1* | | 11/2022 | Ozao | A61B 1/00009 |
| 2023/0149080 A1* | | 5/2023 | Wong | A61B 34/37 |
| | | | | 606/33 |
| 2024/0081611 A1* | | 3/2024 | Shelton, IV | A61B 1/00006 |
| 2024/0423459 A1* | | 12/2024 | Shelton, IV | G16H 40/63 |

FOREIGN PATENT DOCUMENTS

| | | |
|---|---|---|
| CN | 115998421 | 4/2023 |
| DE | 102022127825 | 4/2023 |
| IN | 570971 | 9/2025 |
| JP | H11155869 | 6/1999 |
| JP | 2019505245 | 2/2019 |
| JP | 2021037113 | 3/2021 |
| JP | 7604435 | 12/2024 |
| WO | 2021155319 | 8/2021 |

OTHER PUBLICATIONS

"Japanese Application Serial No. 2022-169393, Office Action mailed Dec. 18, 2023", w English Translation, 18 pgs.

"Japanese Application Serial No. 2022-169393, Decision of Rejection mailed Jun. 10, 2024", w/ English Translation, 15 pgs.

"Japanese Application Serial No. 2024-177187, Notification of Reasons for Rejection mailed Mar. 11, 2025", W English Translation, 8 pgs.

"Japanese Application Serial No. 2022-169393, Response filed Oct. 9, 2024 to Decision of Rejection mailed Jun. 10, 2024", w english claims, 20 pgs.

"Indian Application Serial No. 202244060600, Response filed May 30, 2024 to First Examination Report mailed Jan. 10, 2024", 26 pgs.

"Japanese Application Serial No. 2022-169393, Response filed Mar. 14, 2024 to Office Action mailed Dec. 18, 2023", w english claims, 13 pgs.

"Chinese Application Serial No. 202211302274.7, Office Action mailed May 16, 2025", w/English translation, 23 pgs.

"Chinese Application Serial No. 202211302274.7, Response filed Sep. 16, 2025 to Office Action mailed May 16, 2025", W/English Claims, 17 pgs.

"Indian Application Serial No. 202244060600, Hearing Notice mailed Jul. 31, 2025", 3 pgs.

"Japanese Application Serial No. 2024-177187, Examiners Decision of Final Refusal mailed Aug. 12, 2025", W/ English Translation, 8 pgs.

"Japanese Application Serial No. 2024-177187, Response filed Jun. 11, 2025 to Notification of Reasons for Rejection mailed Mar. 11, 2025", w/ english claims, 7 pgs.

"Indian Application Serial No. 202244060600, Response filed Sep. 16, 2025 to Hearing Notice mailed Jul. 31, 2025", w claims, 6 pgs.

"Japanese Application Serial No. 2024-177187, Response filed Dec. 12, 2025 to Examiners Decision of Final Refusal mailed Aug. 12, 2025", w current English claims, 13 pgs.

* cited by examiner

400

500

600

602 Provide image of the working area

604 Differentiate between tissue and calculi stone

606 Modify suction and/or fluid source

700

702 Capture image of the calculi stone

704 Determine characteristics of the calculi stone

706 Determine treatment plan

ENDOSCOPE LASER-TRIGGERED SUCTION AUTOMATIC ON/OFF

PRIORITY CLAIM

This application claims priority to U.S. Provisional Patent Application Ser. No 63/262,924, filed Oct. 22, 2021, the contents of which are incorporated herein by reference.

BACKGROUND

Medical scopes such as endoscopes were first developed in the early 1800s and have been used to inspect inside the body of a patient. Such scopes can include endoscopes, laparoscopes, ureteroscopes, duodenoscopes, arthroscopes, and others, which can be referred to as endoscopes or scopes. An endoscope may be used to move fluid through an organ. Some endoscopes provide irrigation, suction, or both, such as to move the fluid. Laser energy can also be used inside the body. For example, a laser generator can provide laser energy into the body, such as via a laser fiber or fiber bundle. The laser energy can be used for diagnosis or treatment, such as to perform laser lithotripsy to ablate one or more calculi stones. The ablation can cause the stone to break apart into smaller pieces that can pass naturally or can be grasped, suctioned, or otherwise removed from the body through the endoscope or an ancillary tool.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
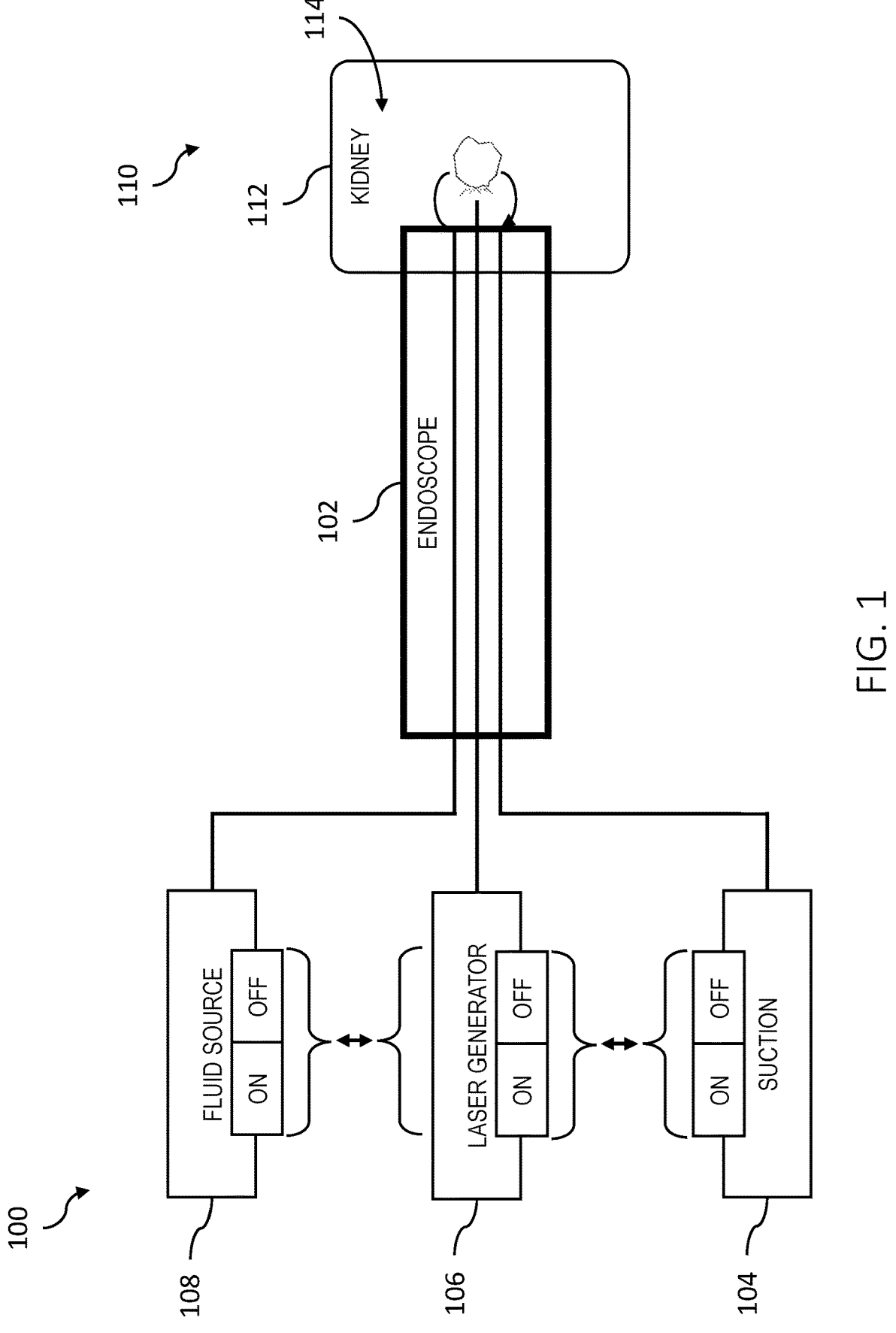
FIG. 1 illustrates an example of portions of an endoscope system with a suction component to control suction and a laser generator.

The systems and techniques described herein relate to medical devices, such as an endoscope, that uses aspiration or "suction" to move fluid, calculi stones, calculi dust and/or calculi fragments, or the like through an organ, such as the kidney, during lithotripsy. The suction of an endoscope can be actuated by, synchronized with, or otherwise coordinated with the laser energy delivery, although the suction may be additionally or alternatively coordinated with one or more additional or different functions. This can be done automatically—without requiring user input to control the suction.

Endoscopes may be used for visualizing an internal target for diagnosis, treatment, or both. An endoscope may be configured to facilitate fluid influx (e.g., "irrigation") and removal (e.g., "suction"), such as to wash away debris from the organ and improve visualization during an endoscopic procedure. For example, a ureteroscope may include an irrigation fluid channel to supply saline to the kidney, and a suction channel to aspirate calculi dust and fragments during a laser lithotripsy procedure. While stone dust and small fragments may be expelled naturally by the patient, it can be beneficial to actively remove the debris during the procedure.

The inflow and outflow of fluid through the kidney may involve increases and decreases in renal pressure that may benefit from monitoring, control, or both. Having suction "on" continuously during an entire procedure may not be desirable, Suction that is always "on" may involve continuous monitoring and control or a continuous inflow of irrigation fluid to replace the fluid removed from suction. Furthermore, when dusting or other stone fragmentation is paused, suction and/or the passage of fluid through the kidney may be unnecessary during that time. Therefore, it is advantageous to control the suction such that it is activated only when needed.

The systems and techniques described herein may be used to activate endoscopic suction at times it is deemed important or desired, and to suspend suction at other times. While suction may be controlled manually by the endoscope user (e.g., using a foot pedal or other actuator), the present systems and techniques can provide a capability to automatically control suction, such as based on one or more criteria such as which do not require a separate direct user input to activate and/or deactivate suction. For example, suction can be automatically controlled based on the state of the laser or other energy source (or an associated control signal), such as being turned on in response to when a laser source is being turned on or is on during laser lithotripsy, and turned off in response to when the laser source is being turned off or is off.

A time shift delay of the suction control relative to the laser generator activation/deactivation may be provided. For example, while the suction could be automatically turned off when the laser is turned off, a programmed turn-off delay may be used to continue the suction for a period of time after the laser is turned off or a period of time before the laser is turned on. For example, the suction may remain "on" for some programmable or otherwise specified amount of time (e.g., ½ second, 1 second, X seconds, etc.) before the laser has begun delivering laser energy or after the laser has stopped delivering laser energy, such as to move the calculi stone or fragments into a desired location for ablation by energy delivery or to provide some amount of time to clear the dust/fragments after the laser activity.

One or more criteria other than time may be used as the basis for automatically delaying when suction will be suspended, such as when an image sensor has produced one or more image(s) that are deemed sufficiently clear of dust, fragments, and/or other debris. For example, a comparison of image clarity, haze, or one or more other individual or composite characteristics may be compared to a specified acceptable amount or a specified acceptable image. This can be carried out algorithmically or using a trained model such as to help determine or improve the results using artificial intelligence and/or machine learning (AI/ML).

For example, the criteria for automatically delaying when suction will be suspended may be based on a sensor-derived measurement of intraoperative pressure. For example, suction may stay on for some time after laser dusting has stopped, depending on when the intraoperative pressure has settled to some acceptable level or range.

Where irrigation or other fluid delivery is based on an active mechanism such as a pump, versus a gravity IV, fluid delivery can be similarly controlled, such as can be based at least in part on one or more laser activation times. For example, both fluid delivery and suction can be automatically suspended (e.g., without requiring any independent direct user input) when laser dusting/fragmentation has ended (or after some delay).

FIG. 1 is a schematic diagram that illustrates an example of portions of an endoscope system 100 with a suction component 104 to control suction and a laser generator 106.

The endoscope system 100 may include an endoscope 102, a suction component 104, a laser generator 106, and fluid source 108. The endoscope system 100 may interact with a patient 110. For example, the endoscope system 110 may be used to access an organ of the patient 110, such as a kidney 112. The kidney 112 may have a calculi stone 114.

The endoscope 102 may include one or more channels, such as a working channel to allow a distal portion of an ancillary device to be introduced to a target site within the patient 110. Separate irrigation and suction channels may be included in the body of the endoscope 102, or such functions may be performed using the working channel of the endoscope 102. Regardless of which channel is used, a distal portion of the suction component 104, a distal portion of a laser fiber from the laser generator 106, or a distal portion of an irrigation channel in fluid communication with the fluid source 108 can be provided with access to the target site within the organ (e.g., kidney 112). The endoscope 102 may include or may be coupled via an illumination fiber or fiber bundle to an illumination light source (which may be different than the laser generator 106). This can help provide a means of illuminating the kidney 112 at the distal end of the endoscope, such as to help visual observation by the endoscope via endoscope visualization optics. The endoscope 102 may be single-use or reusable. The endoscope 102 may be flexible, such as to permit the endoscope 102 to be passed through an incision in the patient 110, through a urethra of the patient 110, or other means of accessing the kidney 112 or other target organ of the patient 110.

The irrigation fluid source 108 may provide saline or other fluid through the endoscope 102 to the procedure site within the kidney 112 or other organ. The fluid source 108 may include an intravenous (IV) bag on a pole that provides fluid due to gravity. Irrigation using the fluid source 108 may be controlled by a pressure cuff, such as that squeezes components of an intravenous bag, by raising or lowering the intravenous bag, by a thumb wheel actuator, such as that adjusts a valve opening of a valve, or other means capable of modifying the rate of providing irrigation or other fluid. The fluid source 108 may be controlled such as to continuously supply fluid. The fluid source 108 may be controlled such as to provide fluid at a constant rate. The fluid source 108 may be controlled such as to provide fluid at an adjustable or even a varying rate. The rate of flow from the fluid source 108 may be controlled manually such as by the endoscope user or another caregiver. The rate of flow from the fluid source 108 may be controlled automatically or semi-automatically, such as based on one or more detected or anticipated events, without requiring user-intervention, although such user-intervention may be permitted.

The laser generator 106 may provide energy through the endoscope 102 to the calculi stone 114, such as via one or more optical fibers or an optical fiber bundle, either of which can be referred to as a laser fiber. For example, the laser generator 106 may generate laser pulses to ablate the calculi stone 114 into smaller pieces (such as dust or fragments) that can be removed from or be passed by the patent 110. The ablation by the laser generator 106 may cause calculi dust or fragments. The calculi dust or fragments may be sized to permit natural passing of the calculi, may be removed using suction applied from the suction component 104, or may be removed with the aid of a retrieval device or other medical equipment. In some embodiments, the laser generator 106 may be substituted for (or augmented by) another energy providing source, such as an ultrasound energy source. The laser generator 106 can be controlled manually by the user to trigger delivery of the laser-energy to the target. Alternatively or additionally, the laser generator 106 may be controlled automatically, e.g., without requiring user intervention to trigger delivery of the laser-energy to the target, such as when an AI/ML or other trained model has identified a calculi stone at which the laser has been aimed. Alternatively or additionally, the laser generator 106 may be controlled semi-automatically, such as when an AI/ML or other trained model has identified a calculi stone at which the laser has been aimed, but requesting user-confirmation before actually triggering delivery of the laser energy. Alternatively or additionally, an energy level of the laser pulses issued by the laser generator 106 or a pulse repetition rate or pattern of the laser generator 106 may be determined automatically or semi-automatically. Such automatic energy level, repetition rate or pattern may be issued automatically, semi-automatically, or may be issued by a user. Controlling any of suction, irrigation, ablation, or other function may be accompanied by control of positioning or movement of endoscope 102 itself, such as in a fully robotic or robotically-assisted approach, or control of one or more other end-effectors associated with the endoscope 102.

The suction component 104 may provide suction through the endoscope 102, such as via a suction channel or a working channel of the endoscope 102, to the target or working area of the organ (e.g., kidney 112). The suction component 104 may remove fluid from the kidney 112 using suction. The suction component 104 may remove calculi dust or fragments from the kidney 112 using suction. The rate of suction may be established or adjusted such as to be substantially similar to the rate of providing irrigation or other fluid, such that the there is a substantially consistent amount of fluid in the working area and the organ. For example, if the fluid delivery rate is high, the suction rate may be high. Similarly, if the fluid rate is low, the suction rate may be low. The fluid delivery rate may be established or modified based at least in part on the suction rate. Conversely, the suction rate may be established or modified based at least in part on the fluid delivery rate.

The endoscope system 100 may include an imaging device, imaging optics, or both. For example, a camera or other imaging device may be incorporated within the endoscope 102. The imaging device may be separate from the endoscope 102—either completely separate, or separate but insertable toward the target via the endoscope 102. The imaging device may provide one or more still or video images of the working area of the organ (e.g., kidney 112). Object recognition or other image-processing may be performed on the images, such as explained herein.

The endoscope system 100 can include or be coupled to a computing device or other controller circuitry that can be implemented in hardware, software, firmware, or some combination of these. The computing device can include a processor and a memory device. The memory device can include instruction that, when performed by the processor, cause the computing device to perform a one or more acts or operations. The computing device may be capable of image processing, activating and/or deactivating the suction component 104, changing a rate of suction of the suction component 104, activating and/or deactivating the laser generator 106, changing an energy level of the laser generator 106, activating and/or deactivating the fluid source 108, changing the fluid delivery rate of the fluid source 108, receiving a sensed indication of one or more characteristics of the working environment from one or more sensors (e.g., a temperature sensor, a pressure sensor, etc.), or a combination thereof.

Figure 2:
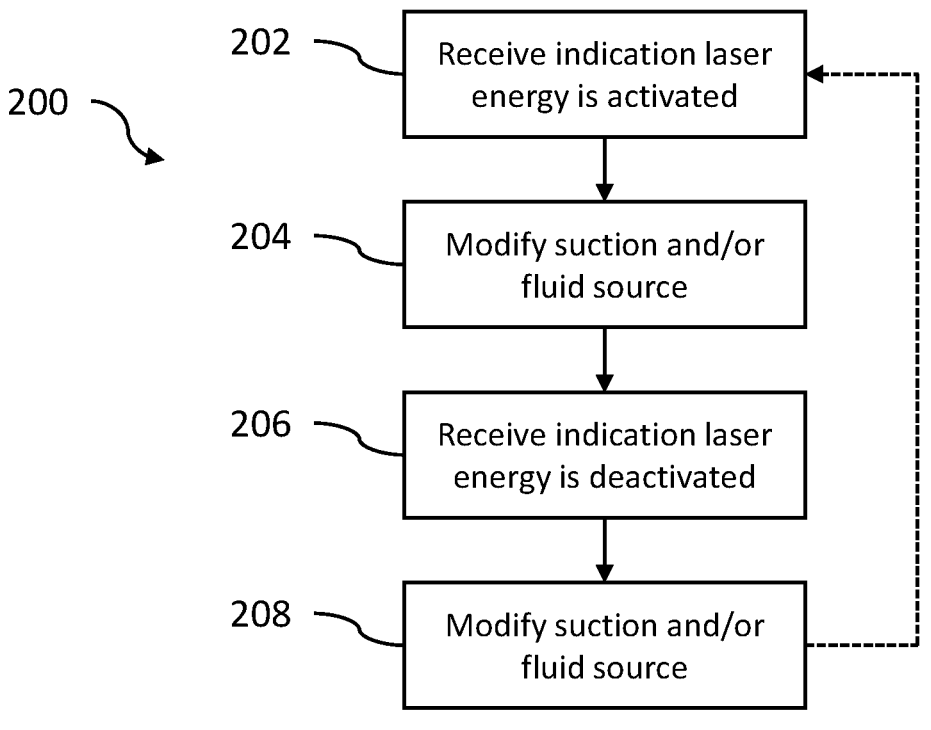
FIG. 2 illustrates an example of a method of controlling suction and/or irrigation based on the laser energy.

FIG. 2 illustrates a method 200 for controlling suction and/or irrigation based on the laser energy. The computing device or controller circuitry may implement method 200. At 202, an indication that the laser generator 106 is activated such that the laser generator 106 is providing laser energy may be received. A user may activate the laser generator 106 to deliver laser energy by direct user input. At 204, suction may be modified. Suction may be modified without direct user input. For example, when the laser generator 106 is providing laser energy, the computing device can, in response, trigger turning on the suction component 104 to provide suction or to increase suction, such as from a lower ambient or standby level of suction. At 206, an indication that the laser generator 106 is deactivated such that the laser generator 106 is not providing laser energy may be received. At 208, suction may be modified. Suction may be modified without additional user input. When the laser generator 106 stops providing laser energy, the computing device can, in response, trigger turning off the suction component 104 to stop providing suction or to reduce suction from a relatively higher "active" suction level to a relatively lower ambient or standby level of suction. The laser generator 106 may stop providing laser energy by direct user input to the laser generator 106. A fluid delivery rate of the fluid source 108 may similarly be automatically controllably adjusted by the computing device in a similar manner to method 200. In an example, one or more parameters associated with the relative energy or power of the laser generator 106 may be additionally or alternatively used, such as to trigger the computing device to change the fluid delivery flow rate of the fluid, the suction flow rate of the suction, or both. For example, lowering the laser energy may trigger the computing device to lower the suction rate of the suction component 104, and raising the laser energy may trigger the computing device to raise the suction rate of the suction component 104. Rather than waiting for the indication that the laser energy is deactivated, the computing device may predict when to modify suction a second time based on a current suction rate, a current fluid rate, a current energy level, and a current pulse pattern of the energy laser. As such, suction can be modified at 204 based on the indication received at 202, and modified at 208 without the additional indication at 206.

Timing of the suction component 104 can also be established or manipulated such as to modify the suction rate and/or to coordinate activation or amount of suction with or in response to the changing or activating/deactivating of the laser generator 106, and need not be coordinated at precisely the same time. For example, the computing device may turn off (or turn down) the suction component 104 at 204 at some difference in time after (or even before) the laser generator 106 has been turned off (or turned down) at 206. For example, the laser generator 106 may have a predetermined pattern of laser energy delivery once laser generator 106 is activated such that the computing device may turn off (or turn down) suction prior to deactivation (or decrease in laser energy) of the laser generator 106. The difference in time may additionally or alternatively be based all or in part on a time delay, a temperature at the working area, a pressure at the working area, and/or other measured characteristic. Thus, the computing device may activate (at 204) or deactivate (at 208) the suction component 104 and/or the fluid source 108 based on a combination of settings or measurements (e.g., temperature, pressure, laser energy, or other measured characteristic). For example, at 202, the laser generator 106 may begin delivering laser energy at time zero, and two seconds later, at 204, the suction component 104 and/or the fluid source 108 may be activated or increased. Similarly, at 206, the laser generator 106 may stop delivering laser energy at time x, and two second later, at 208, the suction component 104 and/or the fluid source 108 may be deactivated or decreased. As another example, the laser generator 106 may be activated, but laser energy may be set to a delay, such that suction may be activated or modified before the delivery of the laser energy. For example, the suction may move the calculi stone 114 into a location for delivery of the laser energy. Method 200 may be repeated as laser generator 106 is activated and deactivated to ablate the calculi stone 114.

Figure 3:
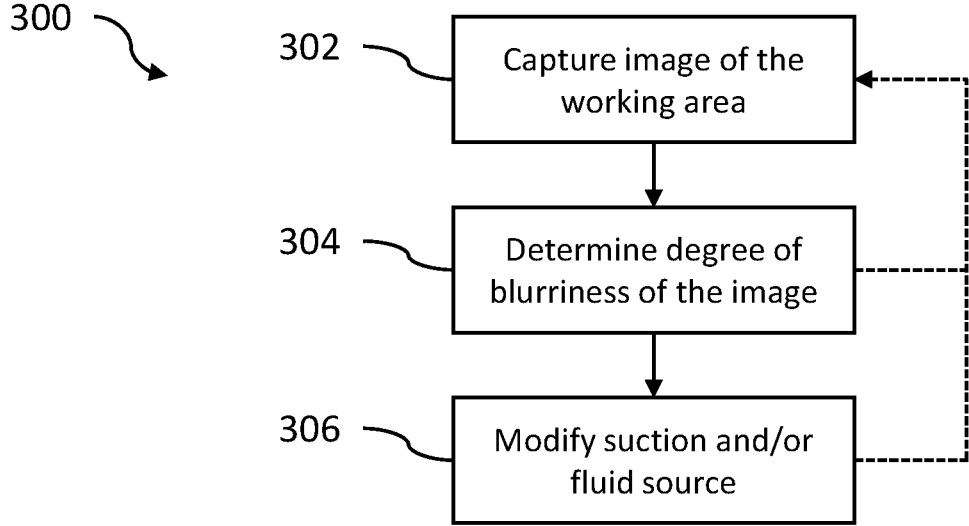
FIGS. 3-6 illustrate example of methods of controlling suction and/or irrigation based on imaging of the working area.

The imaging device can capture one or more images of the working area for the computing device to analyze, such as for using in determining how to automatically or semi-automatically control suction, irrigation, or another operating parameter. FIG. 3 illustrates an example method 300 of controlling suction and/or irrigation based on imaging of the working area. At 302, the imaging device can capture one or more images of the working area. Calculi dust may cause the image to be blurry. At 304, image-processing by the computing device can be used to determine a degree of blurriness of the image. If a certain degree of blurriness is not present, the imaging device can continue to capture images at 302, and the image-progressing device can continue to determine a degree of blurriness of the images at 304. At 306, the computing device can activate the suction component 104 or modify the rate of suction when a certain degree of blurriness is determined to be present in the image. Similarly, the computing device can deactivate the suction component 104 when a lower degree of blurriness is determined to be present in the image. For example, the computing device can compare two or more images of the working area based on the degree of blurriness such as to determine a blurriness trend. The computing device may predict when to activate or deactivate the suction component 104 based on the blurriness trend. Alternatively or additionally, method 300 may be used to control irrigation of fluid source 108 or both irrigation and suction. Method 300, or portions thereof, may be repeated throughout the duration of the procedure. The computing device can compute a composite indicator, such as which can use a degree of blurriness, suction rate, fluid rate, laser energy or status, or one or more indicia of one or more other conditions of the working area to determine or predict when to activate or deactivate the suction component 104.

Figure 4:
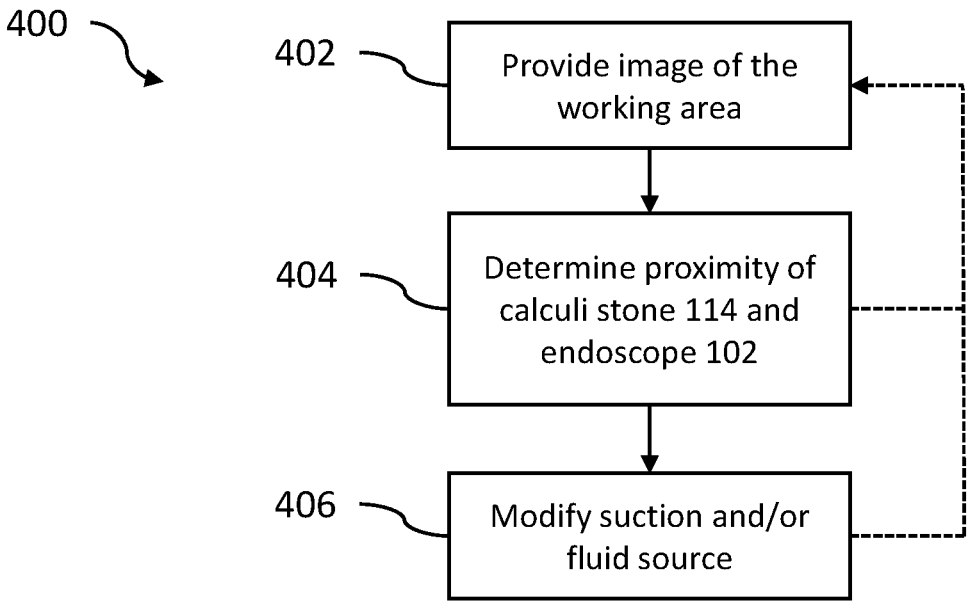

FIG. 4 illustrates an example of a method 400 of controlling suction and/or irrigation based on imaging of the working area. At 402, the imaging device can provide one or more images of the working area. At 404, the computing device can determine or track the proximity between the calculi stone 114, or dust or fragments caused by the calculi stone 114, and a distal end of the endoscope 102. At 406, based on such a distance or proximity determination, the computing device may activate the suction component 104 or modify the rate of suction when a distal end of the endoscope 102 is within a desired distance from the dust or fragments caused by the calculi stone 114. The computing device may deactivate the suction component 104 when a distal end of the endoscope 102 is outside a specified or desired distance from the dust or fragments caused by the calculi stone 114. Alternatively or additionally, method 400 may be used to control irrigation of fluid source 108 or both irrigation and suction. Method 400, or portions thereof, may be repeated throughout the duration of the procedure.

Figure 5:
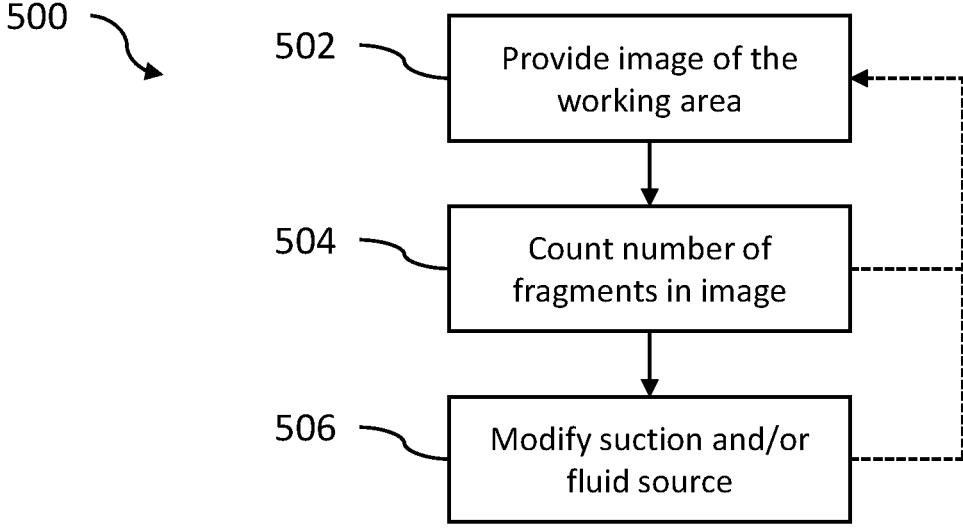

FIG. 5 illustrates an example of a method 500 of controlling suction and/or irrigation based on imaging of the working area. At 502, the imaging device can provide one or more images of the working area. At 504, image-processing by the computing device may be used to count a number of fragments in the image of the working area. Other image-processing may be performed by the computing device such as to determine the size of one or more or each of the fragments. At 506, using this or similar information, the computing device may activate the suction component 104, such as when the number of fragments is greater than a certain number. The computing device may activate the suction component 104 when the size of at least one fragment is below a certain size. For example, the computing device may activate the suction component 104 when the size of at least one fragment is small enough to pass through the endoscope 102, such as through its working channel or a separate suction channel. Additionally or alternatively, using this or similar information, the computing device may issue a control signal to the suction component 104 to deactivate or reduce a suction applied by the suction component 104, such as when the number of fragments is below a certain number. For example, the computing device may issue a control signal to the suction component 104 to deactivate or turn down the suction component 104 when the number of fragments reaches zero. In an example, the computing device may issue a control signal to the suction component 104 to deactivate or turn down the suction component 104 when no fragments are detected that are below a specified threshold size. Alternatively or additionally, method 500 may be used to control irrigation of fluid source 108 or both irrigation and suction. Method 500, or portions thereof, may be repeated throughout the duration of the procedure.

Figure 6:
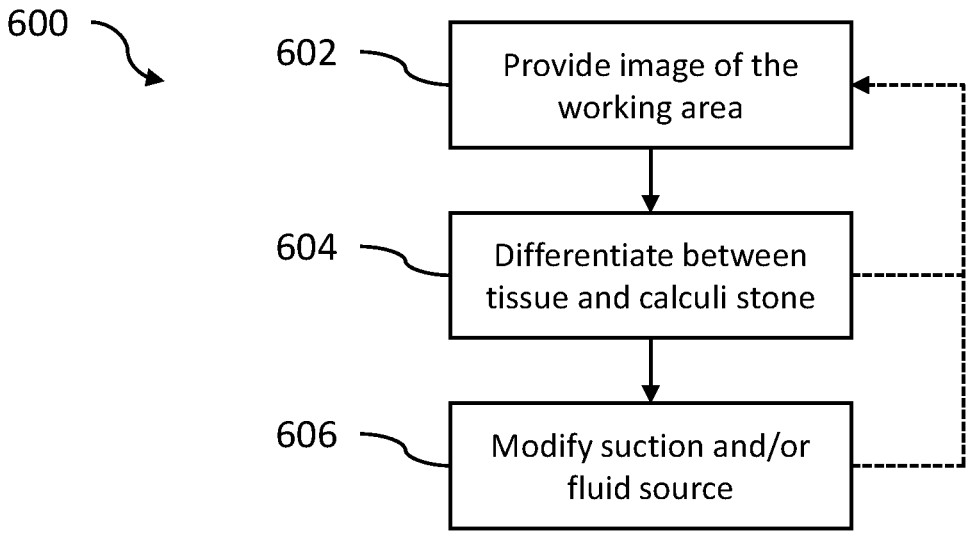

FIG. 6 illustrates an example method 600 of controlling suction and/or irrigation based on imaging of the working area. At 602, the imaging device can provide one or more images of the working area. At 604, image processing by the computing device may be used to differentiate between the calculi stone 114, or dust or fragments of the calculi stone 114, and the organ of the patient. For example, the computing device may determine that the dust or fragments of the calculi stone 114 have settled on the tissue of the organ. If so, at 606, the computing device may issue a control signal to activate the suction component 104 when a distal end of the endoscope 102 is within a certain distance from the dust or fragments of the calculi stone 114, and may issue a control signal to deactivate the suction component 104 when a distal tip of the endoscope 102 is outside of a certain distance of the tissue. For example, the computing device may issue a control signal to deactivate the suction component 104 when the image-processing indicates that the tissue is clear or substantially clear of dust or fragments of the calculi stone 114. Alternatively or additionally, method 600 may be used to control irrigation of fluid source 108 or both irrigation and suction. Method 600, or portions thereof, may be repeated throughout the duration of the procedure.

Figure 7:
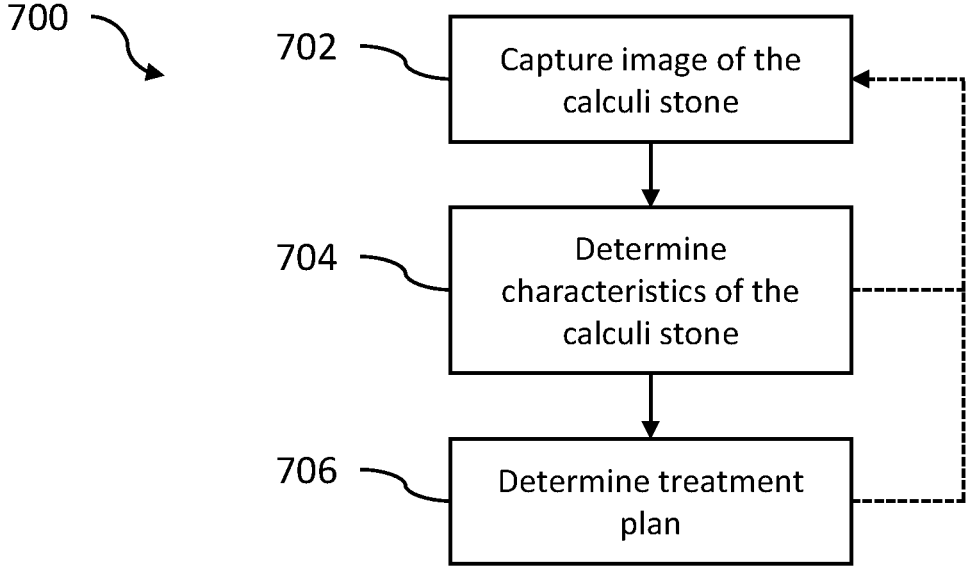
FIG. 7 illustrates an example of a method of determining a treatment plan based on imaging of the calculi stone.

FIG. 7 illustrates an example method 700 of determining a treatment plan based on imaging of the calculi stone 114.

At 702, the imaging device can provide one or more images of the working area, including the calculi stone 114. At 704, the computing device may be programmed to determine one or more characteristics of the calculi stone 114, and/or of the dust or fragments of the calculi stone 114, such as using information from one or more images from the imaging device, or by using spectroscopic information from a response from the target calculi stone 114 to illumination. The computing device may determine a size of the calculi stone 114, and/or of the dust or fragments of the calculi stone 114. The computing device may determine a material composition or property of the calculi stone 114 and/or of the dust or fragments of the calculi stone 114. At 706, based on the one or more characteristics of the calculi stone 114 and/or of the dust or fragments of the calculi stone 114, the computing device may determine a treatment plan. For example, the computing device may determine an energy level of the laser pulses issued by the laser generator 106. As another example, the computing device may determine a pulse repetition rate or pattern of the laser generator 106. As another example, the computing device may determine a suction rate and/or suction pattern of the suction component 104. The computing device may determine a fluid delivery rate and/or fluid delivery pattern of the fluid source 108. Method 700, or portions thereof, may be repeated throughout the duration of the procedure. For example, the treatment plan may be modified throughout the procedure depending on the effectiveness of the present treatment plan. Modification of the treatment plan may include pausing delivery of ablation energy. For example, the treatment may be paused until the image becomes substantially clear and the calculi stone 114 (or the position of the calculi stone 114) can be identified again. The methods described in FIGS. 2-7 may be used independently or in combination.

Figure 8:
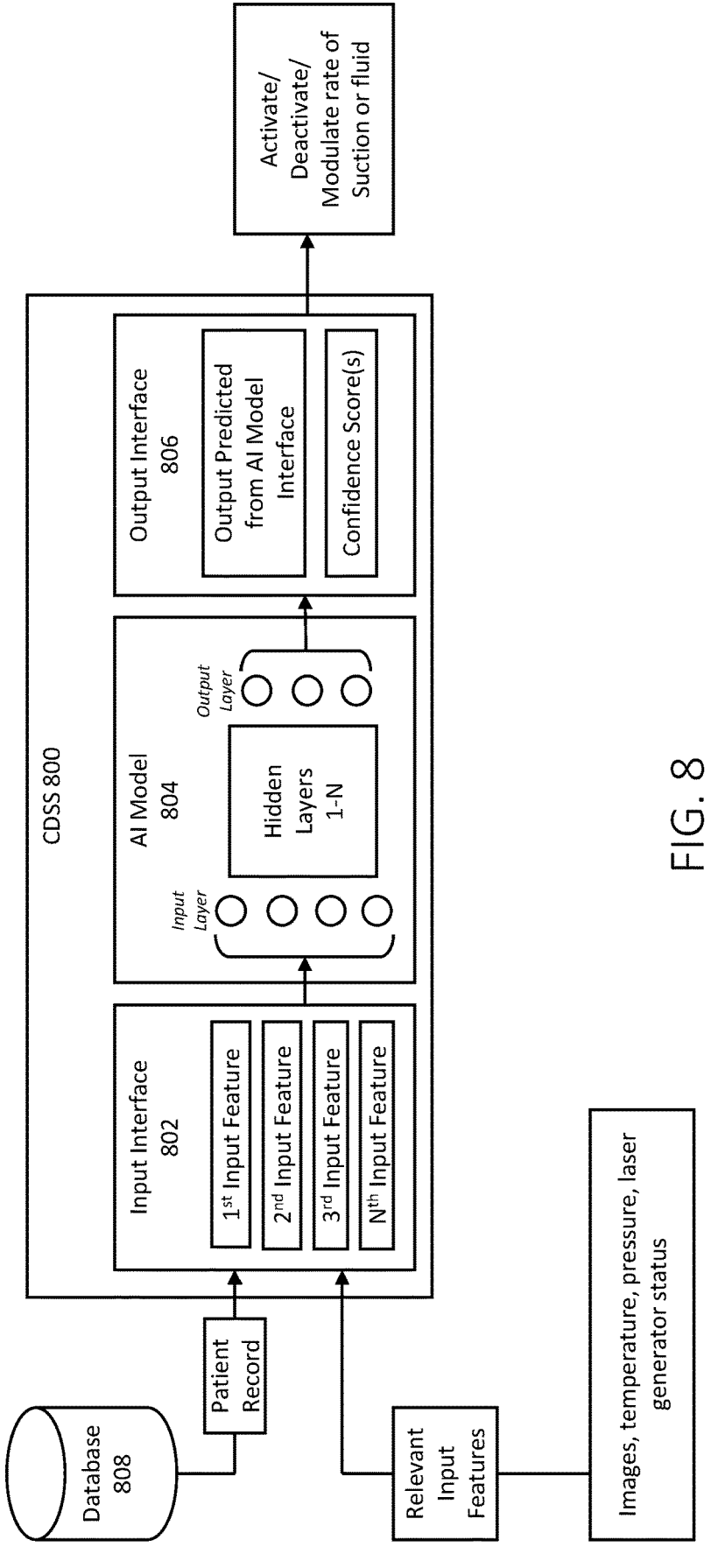
FIG. 8 illustrates an example schematic diagram of an exemplary computer-based clinical decision support system (CRSS).

FIG. 8 shows a schematic diagram of an exemplary computer-based clinical decision support system (CDSS) 800 that is configured to activate fluid or suction, deactivate fluid or suction, modify the rate of fluid flow or suction, or predict when to provide such functions based on laser energy status and/or characteristic information of the working area, such as information about the kidney 112 or the calculi stone 114. Characteristic information may include images, intraoperative temperature, or intraoperative pressure. In various embodiments, the CDSS 800 includes an input interface 802 through which the characteristic information (e.g., images, temperature, pressure) which are specific to a patient are provided as input features to an artificial intelligence (AI) model 804, a processor which performs an inference operation in which the characteristic information (e.g., images, temperature, pressure) are applied to the AI model to generate a control signal to activate, deactivate, or modulate the rate of suction or fluid flow, and a user interface (UI) through which fluid and suction rate and/or status is communicated to a user, e.g., a clinician.

In some embodiments, the input interface 802 may be a direct data link between the CDSS 800 and one or more medical devices that generate at least some of the input features, such as an imaging device, spectroscopic device, thermometer, pressure sensor, or other sensor to provide imaging, spectroscopic, temperature, pressure, or other characteristic information. For example, the input interface 802 may transmit laser energy status and/or characteristic information (e.g., images, temperature, pressure) directly to the CDSS during a therapeutic and/or diagnostic medical procedure. Additionally, or alternatively, the input interface 802 may be a classical user interface that facilitates interaction between a user and the CDSS 800 For example, the input interface 802 may facilitate a user interface through which the user may manually enter a laser energy treatment protocol of the laser generator 106. Additionally, or alternatively, the input interface 802 may provide the CDSS 800 with access to an electronic patient record from which one or more input features may be extracted, such as previous imaging of the working area. In any of these cases, the input interface 802 is configured to collect one or more of the following input features in association with a specific patient on or before a time at which the CDSS 800 is used to assess laser energy status and/or characteristic information of the working area, such as information about the kidney 112 or the calculi stone 114, as described above.

Based on one or more of the above input features, the processor performs an inference operation using the AI model to generate a control signal to activate fluid or suction, deactivate fluid or suction, modify the rate of fluid flow or suction, or predict when to provide such functions. For example, input interface 802 may deliver the image of the working area including the calculi stone 114 into an input layer of the AI model which propagates these input features through the AI model to an output layer. The AI model can provide a computer system the ability to perform tasks, without explicitly being programmed, by making inferences based on patterns found in the analysis of data. AI model explores the study and construction of algorithms (e.g., machine-learning algorithms) that may learn from existing data and make predictions about new data. Such algorithms operate by building an AI model from example training data in order to make data-driven predictions or decisions expressed as outputs or assessments.

There are two common modes for machine learning (ML): supervised ML and unsupervised ML. Supervised ML uses prior knowledge (e.g., examples that correlate inputs to outputs or outcomes) to learn the relationships between the inputs and the outputs. The goal of supervised ML is to learn a function that, given some training data, best approximates the relationship between the training inputs and outputs so that the ML model can implement the same relationships when given inputs to generate the corresponding outputs. Unsupervised ML is the training of an ML algorithm using information that is neither classified nor labeled, and allowing the algorithm to act on that information without guidance. Unsupervised ML is useful in exploratory analysis because it can automatically identify structure in data.

Common tasks for supervised ML are classification problems and regression problems. Classification problems, also referred to as categorization problems, aim at classifying items into one of several category values (for example, is this object an apple or an orange?). Regression algorithms aim at quantifying some items (for example, by providing a score to the value of some input). Some examples of commonly used supervised-ML algorithms are Logistic Regression (LR), Naive-Bayes, Random Forest (RF), neural networks (NN), deep neural networks (DNN), matrix factorization, and Support Vector Machines (SVM).

Some common tasks for unsupervised ML include clustering, representation learning, and density estimation. Some examples of commonly used unsupervised-ML algorithms are K-means clustering, principal component analysis, and autoencoders.

Another type of ML is federated learning (also known as collaborative learning) that trains an algorithm across multiple decentralized devices holding local data, without exchanging the data. This approach stands in contrast to traditional centralized machine-learning techniques where all the local datasets are uploaded to one server, as well as to more classical decentralized approaches which often assume that local data samples are identically distributed. Federated learning enables multiple actors to build a common, robust machine learning model without sharing data, thus allowing to address critical issues such as data privacy, data security, data access rights and access to heterogeneous data.

In some examples, the AI model may be trained continuously or periodically prior to performance of the inference operation by the processor. Then, during the inference operation, the patient specific input features provided to the AI model may be propagated from an input layer, through one or more hidden layers, and ultimately to an output layer that corresponds to the control signal to activate fluid or suction, deactivate fluid or suction, modify the rate of fluid flow or suction, or predict when to provide such functions. For example, the AI model 804 may be trained to implement the methods described in any of FIG. 2-7, alone or in combination.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMS), read only memories (ROMs), and the like.

What is claimed is:

1. An endoscopic system for coordinating operation of an ablation modality with at least one of an ancillary suction or irrigation modality, the endoscopic system comprising:

controller circuitry, configured to issue at least two control signals to coordinate a timing or other parameter of at least one of the ancillary suction or irrigation modality with an ablation timing or other ablation parameter of ablation energy issued by the ablation modality toward an ablation target within a patient, wherein:

the at least two control signals are issued automatically, without requiring direct user input to control the at least one of the ancillary suction or irrigation modality, to provide a relative increase of at least one of suction or irrigation in temporal coordination with issuance of the ablation energy by the ablation modality; and the controller circuitry is configured to predict a duration between a first control signal and a second control signal based on at least one of: i) spectroscopic or other characteristic information about the ablation target, or ii) one or more ablation parameters.

2. The endoscopic system of claim 1, further comprising:

at least one of an imaging device, spectroscopic device, or other sensor to provide the spectroscopic or other characteristic information about the ablation target and imaging, spectroscopic, or other characteristic information about an ablation target environment within the patient wherein;

the controller circuitry generates the at least two control signals based at least in part on information from at least one of the imaging device, spectroscopic device, or the other sensor about at least one of the ablation target within the patient or the ablation target environment within the patient.

3. The endoscopic system of claim 2, wherein the controller circuitry:

receives, from the imaging device, a first image of the ablation target environment;

identifies dust or fragments of the ablation target from the first image; and generates one or both of the at least two control signals based on characteristic information about the dust or fragments identified in the first image.

4. The endoscopic system of claim 3, wherein the characteristic information about the dust or fragments identified in the first image is a degree of blurriness caused by the dust of the ablation target in the first image.

5. The endoscopic system of claim 3, wherein the characteristic information about the dust or fragments identified in the first image is a number of fragments of the ablation target in the first image.

6. The endoscopic system of claim 3, wherein the characteristic information about the dust or fragments identified in the first image is an amount of dust or fragments of the ablation target settled in the ablation target environment in the first image.

7. The endoscopic system of claim 3, wherein the controller circuitry:

receives, from the imaging device, a second image of the ablation target environment;

identifies dust or fragments of the ablation target from the second image; and generates one or both of the at least two control signals based on characteristic information about the dust or fragments identified in the second image.

8. The endoscopic system of claim 7, wherein the characteristic information about the dust or fragments identified in the second image is a change in a degree of blurriness caused by the dust of the ablation target between the first image and the second image.

9. The endoscopic system of claim 7, wherein the characteristic information about the dust or fragments identified in the second image is a trend in a degree of blurriness caused by the dust of the ablation target based on the first image and the second image.

10. The endoscopic system of claim 9, wherein the controller circuitry predicts when to generate the at least two control signals based on the trend in the degree of blurriness caused by the dust of the ablation target based on the first image and the second image.

11. The endoscopic system of claim 7, wherein the characteristic information about the dust or fragments identified in the second image is a change in a number of fragments of the ablation target between the first image and the second image.

12. The endoscopic system of claim 7, wherein the characteristic information about the dust or fragments identified in the second image is a change in an amount of dust or fragments of the ablation target settled in the ablation target environment between the first image and the second image.

13. The endoscopic system of claim 2, wherein the imaging, spectroscopic, or other characteristic information about the ablation target environment within the patient is an intraoperative pressure or intraoperative temperature of the ablation target environment.

14. The endoscopic system of claim 2, wherein the controller circuitry predicts the duration between the first control signal and the second control signal based further on the imaging, spectroscopic, or other characteristic information about the ablation target environment within the patient.

15. The endoscopic system of claim 1, wherein the control signal to coordinate the timing or other parameter of at least one of the ancillary suction or irrigation modality with the ablation timing or other ablation parameter of ablation energy issued by the ablation modality is issued with a temporal shift from the ablation timing of ablation energy.

16. A method for coordinating operation of an ablation modality with at least one of an ancillary suction or irrigation modality, the method comprising:

issuing at least two control signals to coordinate a timing or other parameter of at least one of the ancillary suction or irrigation modality with an ablation timing or other ablation parameter of ablation energy issued by the ablation modality toward an ablation target within a patient, wherein;

the at least two control signals are issued automatically, without requiring direct user input to control the at least one of the ancillary suction or irrigation modality, to provide a relative increase of at least one of suction or irrigation in temporal coordination with issuance of the ablation energy by the ablation modality; and predicting a duration between a first control signal and a second control signal based on at least one of: i) spectroscopic or other characteristic information about the ablation target, or ii) one or more ablation parameters.

17. The method of claim 16, further comprising:

receiving, via at least one of an imaging device, spectroscopic device, or other sensor, the spectroscopic or other characteristic information about the ablation target and imaging, spectroscopic, or other characteristic information about an ablation target environment within the patient; and generating the at least two control signals based at least in part on information from at least one of the imaging device, the spectroscopic device, or the other sensor about at least one of the ablation target within the patient or the ablation target environment within the patient.

18. The method of claim 17, further comprising:

receiving a first image of the ablation target environment;

identifying dust or fragments of the ablation target from the first image; and generating one or both of the at least two control signals based on characteristic information about the dust or fragments identified in the first image.

19. The method of claim 18, wherein the characteristic information about the dust or fragments identified in the first image is a degree of blurriness caused by the dust of the ablation target in the first image.

20. The method of claim 18, wherein the characteristic information about the dust or fragments identified in the first image is a number of fragments of the ablation target in the first image.

21. The method of claim 18, wherein the characteristic information about the dust or fragments identified in the first image is an amount of dust or fragments of the ablation target settled in the ablation target environment in the first image.

22. The method of claim 18, further comprising:
receiving a second image of the ablation target environment;
identifying dust or fragments of the ablation target from the second image; and
generating one or both of the at least two control signals based on characteristic information about the dust or fragments identified in the second image.

23. The method of claim 22, wherein the characteristic information about the dust or fragments identified in the second image is a change in a degree of blurriness caused by the dust of the ablation target between the first image and the second image.

24. The method of claim 22, wherein the characteristic information about the dust or fragments identified in the second image is a trend in a degree of blurriness caused by the dust of the ablation target based on the first image and the second image.

25. The method of claim 24, further comprising:
predicting when to generate the at least two control signals based on the trend in the degree of blurriness caused by the dust of the ablation target based on the first image and the second image.

26. The method of claim 22, wherein the characteristic information about the dust or fragments identified in the second image is a change in a number of fragments of the ablation target between the first image and the second image.

27. The method of claim 22, wherein the characteristic information about the dust or fragments identified in the second image is a change in an amount of dust or fragments of the ablation target settled in the ablation target environment between the first image and the second image.

28. The method of claim 17, wherein the imaging, spectroscopic, or other characteristic information about the ablation target environment within the patient is an intraoperative pressure or intraoperative temperature of the ablation target environment.

29. An endoscopic system for coordinating operation of an ablation modality with at least one of an ancillary suction or irrigation modality, the endoscopic system comprising:
controller circuitry, configured to issue a treatment plan to coordinate a timing or other parameter of an ablation timing or other ablation parameter of ablation energy issued by the ablation modality toward an ablation target within a patient; and
at least one of an imaging device, spectroscopic device, or other sensor to provide imaging, spectroscopic, or other characteristic information about at least one of the ablation target within the patient or an ablation target environment within the patient wherein:
the treatment plan includes generating at least two control signals to coordinate the ablation timing or other ablation parameter of ablation energy issued by the ablation modality with a timing or other parameter of at least one of the ancillary suction or irrigation modality;
the controller circuitry is configured to predict a duration between a first control signal and a second control signal based on at least one of: i) spectroscopic or other characteristic information about the ablation target, or ii) one or more ablation parameters; and
the controller circuitry generates the treatment plan based at least in part on information from at least one of the imaging device, spectroscopic device, or the other sensor about at least one of the ablation target within the patient or an ablation target environment within the patient.

30. The endoscopic system of claim 29, wherein the controller circuitry:
receives, from the imaging device, a first image of the ablation target environment;
identifies dust or fragments of the ablation target from the first image; and
generates one or both of the at least two control signals based on characteristic information about the dust or fragments identified in the first image.

* * * * *